(12) United States Patent
White et al.

(10) Patent No.: US 9,943,487 B2
(45) Date of Patent: Apr. 17, 2018

(54) POLYDOPAMINE-COATED CAPSULES

(71) Applicant: The Board of Trustees of the University of Illinois, Urbana, IL (US)

(72) Inventors: Scott R. White, Champaign, IL (US); Nancy R. Sottos, Champaign, IL (US); Sen Kang, Oakdale, MN (US); Marta B. Baginska, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/165,520

(22) Filed: May 26, 2016

(65) Prior Publication Data
US 2016/0346217 A1     Dec. 1, 2016

Related U.S. Application Data

(60) Provisional application No. 62/166,575, filed on May 26, 2015.

(51) Int. Cl.
*A61K 9/48* (2006.01)
*A61K 31/137* (2006.01)

(52) U.S. Cl.
CPC .......... *A61K 9/4891* (2013.01); *A61K 31/137* (2013.01)

(58) Field of Classification Search
None
See application file for complete search history.

(56) References Cited

U.S. PATENT DOCUMENTS

| | | | |
|---|---|---|---|
| 5,100,802 A * | 3/1992 | Mickols | G01N 21/6408 436/172 |
| 6,518,330 B2 | 2/2003 | White et al. | |
| 6,858,859 B2 | 2/2005 | Kusunose | |
| 7,192,993 B1 | 3/2007 | Sarangapani et al. | |
| 7,566,747 B2 | 7/2009 | Moore et al. | |
| 7,569,625 B2 | 8/2009 | Keller et al. | |
| 7,723,405 B2 * | 5/2010 | Braun | B29C 73/163 523/212 |
| 8,846,404 B2 | 9/2014 | Odom et al. | |
| 8,951,639 B2 | 2/2015 | White et al. | |
| 9,108,364 B2 | 8/2015 | Caruso et al. | |
| 2008/0299391 A1 | 12/2008 | White et al. | |
| 2011/0293958 A1 | 12/2011 | Benkoski et al. | |
| 2012/0237605 A1 | 9/2012 | Messersmith et al. | |
| 2013/0017405 A1 | 1/2013 | Benkoski et al. | |

(Continued)

FOREIGN PATENT DOCUMENTS

| | | |
|---|---|---|
| CN | 101966441 A | 2/2011 |
| CN | 102861921 B | 1/2016 |

OTHER PUBLICATIONS

Kang et al., ACS Appl. Mater. Interfaces, 2015, vol. 7, pp. 10952-10956.*

(Continued)

*Primary Examiner* — Brian Gulledge
(74) *Attorney, Agent, or Firm* — Haukaas Fortius PLLC; Michael H. Haukaas

(57) ABSTRACT

One aspect of the invention is a polymer material comprising a capsule coated with PDA. In certain embodiments, the capsule encapsulates a functional agent. The encapsulated functional agent may be an indicating agent, healing agent, protecting agent, pharmaceutical drug, food additive, or a combination thereof.

23 Claims, 8 Drawing Sheets

(56) References Cited

U.S. PATENT DOCUMENTS

2014/0272364 A1* 9/2014 Fitz ..................... C23F 11/149
428/220
2014/0363091 A1 12/2014 Boday et al.

OTHER PUBLICATIONS

Lynge et al., Nanoscale, 2011, vol. 3, pp. 4916-4928.*
Jin, Henghua et al., "Self-Healing Thermoset Using Encapsulated Epoxy-Amine Healing Chaemistry," Polymer (2012) doi:10.1016/j.polymer.2011.12.005, pp. 1-7.
Jin, Henghua et al., "Thermally Stable Autonomic Healing in Epoxy Using a Dual-Microcapsule System," Advanced Materials, 2013, p. 1-6.
Jones, A.R. et al., "Full Recovery of Fiber/Matrix Interfacial Bond Strength Using a Microencapsulated Solvent-Based Healing System," Composites Science and Technology, 79 (2013) pp. 1-7.
Lynge, Martin E. et al., "Polydopamine—A Nature-Inspired Polymer Coating for Biomedical Science," Nanoscale, 2011, 3, pp. 4916-4928.
Rtoy, Myung-Hyun et al., "Mussel-Inspired Adhesive Binders for High-Performance Silicon Nanoparticle Anodes in Lithium-Ion Batteries," Advanced Materials, 2013, 25, pp. 1571-1576.
Si J. et al., "Preparation and Characterization of Bio-Compatible FE3O4@Polydopamine Spheres With Core/Shell Nanostructure," Materials Chemistry and Physics, 2011, vol. 128, No. 3.
Yu, B., et al. "Robust Polydopamine Nano/Microcapsules and Their Loading and Release Behavior," Chem. Commun., 2009, 6789-6791, Chinese Academy of Sciences, Lanzhou.

* cited by examiner (a)

(b)

POLYDOPAMINE-COATED CAPSULES

RELATED APPLICATIONS

This application claims priority under 35 U.S.C. § 119(e) to U.S. Provisional Patent Application No. 62/166,575, filed May 26, 2015, which is incorporated herein by reference.

GOVERNMENT SUPPORT

This invention was made with government support under ANL 9F-3192 EFRC awarded by the United States Department of Energy. The government has certain rights in the invention.

BACKGROUND OF THE INVENTION

Nanocapsules and microcapsules are useful for encapsulating a variety of functional core contents, such as indicating agents, healing agents, corrosion inhibitors, pharmaceutical drugs, food additives, and paints. Blaiszik et al., *Annu. Rev. Mater. Res.* 2010, 40, 179-211; White et al., *Nature* 2001, 409, 794-797; Esser-Kahn et al., *Macromolecules* 2011, 44, 5539-5553. Many of the capsules have a solid polymeric shell wall and encapsulate a functional liquid agent core. The capsules are designed to perform when they are exposed to certain intended stimuli, which rupture or disintegrate the shell wall of the capsule and releases the functional agent contained therein to fulfill its function. Jones et al., *Compos. Sci. Technol.* 2013, 79, 1-7; Cho et al., *Adv. Mater.* 2009, 21, 645-649; Yuan et al., *Macromolecules* 2008, 41, 5197-5202.

In many applications, the capsules may be stored or used for a long period of time before being needed to perform their intended function. Patel et al., *Composites Part A: Appl. Sci. Manuf.* 2010, 41, 360-368. The capsules may also be exposed to severe conditions that could potentially compromise the integrity of the capsules and cause premature rupturing of the shell wall and release of the core content. Any loss of core content prior to intended stimuli exposure, such as during storage, manufacturing, or service, can lead to reduced beneficial effects of the encapsulated systems in their application. Jin et al., *Polymer* 2012, 53, 581-587. When capsules are exposed to harsh environments, such as elevated temperature or strong solvents, the capsule shell wall may degrade and accelerate diffusion of the core content due to chemical gradients. In self-healing polymers, high processing temperatures (>100° C.) may cause core diffusion to the host matrix, reducing self-healing capability. Jin et al., *Adv. Mater.* 2014, 26, 282-287. Additionally, wet processing in polymeric composite fabrication often involves strong solvents that can degrade the capsule shell wall. Yuan et al., *Mater. Chem. Phys.* 2008, 110, 417-425.

The stability of poly(urea formaldehyde) (UF) shell wall microcapsules at different temperatures has been studied. Yuan et al., *J. Mater. Sci.* 2007, 42, 4390-4397. This article shows that microcapsules start to dimple at 120° C. for 2 hours due to the diffusion of the liquid core content (a mixture of butyl glycidyl ether and diglycidyl ether of bisphenol A) from the microcapsule shell wall. Diffusion of core content was also observed when the microcapsules were immersed in acetone solvent. Double layered core-shell microcapsules have been prepared by condensing urea-formaldehyde (UF) resin on as-prepared polyurethane (PU) microcapsule surfaces. Li et al., *Polym. Bull.* 2008, 60, 725-731. Subsequently, an improved single-batch process has been described for the preparation of PU/UF double layered microcapsules by adding PU prepolymer into the liquid core phase and allowing PU interfacial polymerization for inner PU shell wall formation at the same time as outer UF formation. Caruso et al., *ACS Appl. Mater. Interfaces* 2010, 2, 1195-1199. Though increased thermal stability has been observed with this process, the microcapsules still exhibited moderate core content loss at elevated temperatures (~10 wt % loss at 180° C. for 2 h). Furthermore, the stability of the microcapsules in harsh environments (e.g., in strong solvents) was not evaluated in this article.

In self-healing polymer applications, small size-scale self-healing of sub-micron crack sizes has motivated the realization of sub-micron microcapsules. As the size of microcapsules decrease, the microcapsule shell wall thickness also decreases (from ca. 300 nm of 250 µm diameter microcapsules to ca. 50 nm of ca. 2 µm diameter microcapsules). Therefore, the stability of small size microcapsules becomes a concern. Another study reported a technique to coat a 20-40 nm thick silica layer on microcapsule surfaces for improved environmental stability. Jackson et al., *Macromol. Rapid Commun.* 2011, 32, 82-87. To address the fragility of small size microcapsules, this study developed a silica coating technique to coat 20-40 nm thick silica onto microcapsule surfaces and dispersed the microcapsules in an epoxy matrix. However, two problems were observed with this process—relatively poor interfacial adhesion between the inorganic silica and the organic epoxy matrix and an increased stiffness of the microcapsules imparted by the silica coating. In self-healing applications, the low adhesion strength and high stiffness may lead to deflection of the crack from the microcapsules instead of rupturing the microcapsules as the crack propagates. Thus, the silica coated capsules may hinder or prevent the release of the functional core content when damage occurs.

Polydopamine (PDA) is an important polymer formed by the oxidation of dopamine. It is commonly used for coating various surfaces and recently has been applied in the biomedical field, for example, from coatings for interfacing with cells, to drug delivery and biosensing. Lynge et al., *Nanoscale*, 2011, 3, 4916-4928. The coexistence of catechol and amine groups found in proteins of mussels is believed to provide strong adhesion properties. Dopamine is a building block that contains both catechol and amine moieties. As a result, the polymeric form of dopamine, PDA, shows strong adhesion to many types of surfaces. Lee et al., *Science* 2007, 318, 426-430; Ryou et al., *Adv. Mater.* 2013, 25, 1571-1576. Under basic conditions, dopamine immediately undergoes polymerization and deposits on the target surface as PDA. Dreyer et al., *Chem. Sci.* 2013, 4, 3796. Though the detailed structure of PDA remains elusive, recent investigations have indicated that hydrogen bonding and π-π stacking make PDA a dense membrane with remarkable stability. Dreyer et al., *Langmuir* 2012, 28, 6428-6435; Liebscher et al., *Langmuir* 2013, 29 (33), 10539-10548.

Bio-compatible and superparamagnetic $Fe_3IO_4$/Polydopamine nanocomposites have been synthesized for use in catalyst supports and drug delivery. Si et al., *Materials Chemistry And Physics,* 2011, vol. 128, no. 3. Chinese patent application number CN102861921A describes a method of synthesizing magnetic/gold nanoparticles with $Fe_3O_4$/PDA for use in drug delivery. Chinese patent application number CN101966441A describes a method of synthesizing microcapsules with calcium carbonate particles and PDA, then removing the calcium carbonate to provide a hollow microcapsule. US patent application publication number US 2012/0237605A describes nanoparticles with a gold, silver or iron oxide metallic core and a PDA coating. The loading and release behavior of PDA capsules have also been evaluated. Yu et al., *Chem. Commun.*, 2009, 6789-6791.

Notwithstanding the advances in the capsule field, there remains a need to prepare improved capsules that are stable and robust. Given the sophistication of recent advances being utilized in capsule technology and the growing trend to utilize capsules, this need is more urgent than ever. Accordingly, there is a need for a more stable capsule that can withstand a wide variety of manufacturing, processing, servicing and environmental conditions. In particular, there is a need for environmentally stable capsules containing liquid functional agents. An optimum capsule would be stable over a wide spectrum of environmental conditions and be able to store the core content over an extended period before a triggering mechanism is activated.

SUMMARY

Polydopamine (PDA) is a compliant polymer containing amine and catechol moieties that exhibit strong bonding to a wide variety of surfaces. A protective barrier on the capsule is important to limit or inhibit core content diffusion and premature shell wall rupture. The physical interactions of functional units and polymer chains provided by PDA (e.g., aromatic π-π stacking and hydrogen bonding) contribute to making a virtually impermeable membrane on the capsule with remarkable stability. By coating the capsules with a protective PDA layer, the capsule stability (e.g., thermal and solvent stability) is significantly enhanced compared to uncoated capsules and conventional capsules (e.g., silica coated microcapsules in micron-scale self-healing applications). A PDA coating enhances the integrity of the capsule, which allows a skilled artisan to provide an improved capsule delivery system of liquid core content to a targeted surface or location via capsule rupture upon exposure to intended stimuli.

One aspect of the invention is a polymer material comprising a capsule coated with PDA. In certain embodiments, the capsule encapsulates a functional agent. The encapsulated functional agent may be an indicating agent, healing agent, protecting agent, pharmaceutical drug, food additive, or a combination thereof. The PDA is coated on at least one shell wall of the capsule. The shell wall may comprise standard materials, such as a single wall made out of poly(urea formaldehyde) (UF) or a dual wall made out of poly(urea formaldehyde)/poly(urethane) (PUF/PU). Other materials may also be used for the shell wall, such as polystyrene and polyvinyl chloride.

Another aspect is an autonomic self-indicating, self-healing and/or self-protecting polymer material having a plurality of capsules dispersed therein, the capsules having an indicating, healing and/or protecting agent encapsulated therein and at least one layer of a shell wall coated with PDA, where the self-indicating, self-healing and/or self-protecting process can be initiated when a region of the polymer material has been sufficiently damaged so as to rupture one or more capsules, which thereby releases the indicating, healing and/or protecting agent in the damaged region.

Another embodiment of the invention is a polymer material comprising one or more film-forming binders and a plurality of capsules, the capsules enclosing at least a functional agent encapsulated within a volume defined by an outer shell, where at least one layer of the outer shell is coated with PDA, and where the functional agent can be released to perform its intended function when a region of the polymer material has been exposed to certain stimuli that sufficiently damages and ruptures one or more capsules.

Also provided in this disclosure is a method of coating polydopamine onto a shell wall of a capsule by oxidizing dopamine in an aqueous basic buffer solution (e.g., >pH 7) or by adding an oxidant in an aqueous buffer solution having an acidic or about neutral pH (e.g., <pH 7), whereby the dopamine polymerizes on the shell wall of the capsule, and drying the capsule.

The PDA coated capsules described herein provide exceptional stability and protection to the capsules and can be employed in a wide variety of applications.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
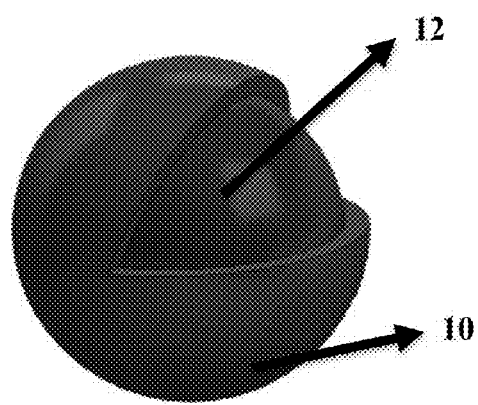
FIG. 1 shows a capsule with a cutout to view the core content encapsulated therein.

A major drawback of capsule technology is capsule fragility and lack of stability. The present invention addresses these limitations and is relevant in all fields that utilize capsules. Previously, PDA has been used on solid nanoparticles and in conjunction with calcium carbonate to form hollow capsules. In this disclosure, we teach how to use PDA on capsules containing functional agent(s), which provides improved protection and stability to the capsules. The PDA coating on the capsules also improve their processability as it can hinder or prevent agglomeration (e.g., clumping together) of the capsules. This is an advantage for many applications and allows for an even dispersion of capsules in a coating (e.g., epoxy), even after a prolonged time in storage.

The PDA is coated onto a shell wall of the capsule. In an embodiment, a plurality of capsules and dopamine are mixed in an aqueous basic buffer solution, whereby the dopamine polymerizes on the shell wall of the capsule. The pH of the basic buffer solution is greater than 7. In embodiments, the pH is greater than about 7.5 or 8. In a particular embodiment, the pH is about 8.4. In an alternative method, a plurality of capsules and dopamine are mixed in an aqueous acidic or about neutral buffer solution, and an oxidant (e.g., ammonium persulfate) is added to the buffer solution, whereby the dopamine polymerizes on the shell wall of the capsule. The pH of the acidic or about neutral buffer solution is about less than or equal to 7. In embodiments, the pH is about 2-7, 3-7, 4-7, 5-7, 6-7, or 7.

The capsules may be nano or micro in size. For example, the capsules may be about 200 nm to 1 mm in size. The capsules may be single-walled or multi-walled capsules. The PDA is coated onto at least one wall of the capsules. Usually, the PDA coating will be deposited on the outer wall of the capsule. However, in some embodiments, one or more additional materials may be coated on top of and/or below the PDA layer. Our experimental observations show that the thermal stability of PU/UF double layered microcapsules is dependent on the wall thickness and size of the microcapsules. The thermal stability decreases dramatically as the dimensions of the microcapsule decrease due to the thinner microcapsule shell wall. Accordingly, PDA coated capsules are very useful for protecting small dimensioned microcapsules.

The functional agent is selected based on the intended application. For example, in the biomedical field, the functional agent may be a pharmaceutical drug or a nutraceutical, such as a solid or liquid food supplement. The functional agent is generally in liquid form, but may also be a solid suspension or emulsion. Often, a functional agent is dissolved in a solvent. Single and multi-part functional agents may be utilized. For example, one type of capsules can contain agent A and another type of capsules can contain agent B. When the two types of capsules rupture or disintegrate, they will release agents A and B to react in the intended area. The functional agents may be used in all kinds of coatings—primers, mid-coats, and top-coats. The functional agents may be combined with other functionalized coatings, such as agents and coatings to improve or provide various different properties of the coating (e.g., hydrophobicity, ice repellence, anti-fouling, anti-dusting, anti-corrosion, indicators of damage, thermo-protection, etc.).

In some embodiments, the functional agent is an indicating agent that may be used to signify damage in polymeric coatings and biomolecules. The indicating agent may be a color indicator (e.g., dye), such as 2',7'-dichlorofluorescein (DCF) or bromophenol blue (BPB), which when released from the capsule can react with free and/or residual amines that are present in or added to the area to form a colored product. Different mechanisms may be employed with other dyes, such as Neutral Red. In a two-component system, an acid/base reaction may be utilized to produce a color change. In certain embodiments, multi-component color indicators are encapsulated (e.g., a reaction based on at least two chemicals used to generate the indicating color). For instance, U.S. Pat. No. 8,846,404 describes a self-indicating polymeric coating where damage-induced rupturing of microcapsules initiates a reaction between a charge-transfer donor and a charge-transfer acceptor to form a colored charge-transfer product in the damaged area. In another aspect, the capsules are employed with multiple functional agents. For example, a polymer coating or composite can contain capsules having a healing agent, a primary color indicator, and a secondary color indicator. When the capsules rupture, the primary color indicator will show that damage has occurred, the healing agent will repair the damaged area, and the secondary color indicator will show that the damaged area has been repaired.

Healing agents are employed in many industries. Self-healing coatings are used extensively in many products, such as in articles of manufacture in the military, aerospace and petroleum industries. Examples of these approaches are described in U.S. Pat. Nos. 9,108,364, 7,723,405, 7,569,625, 7,566,747, 7,192,993, 6,858,859, and 6,518,330, and U.S. Patent Publication Numbers 2014/0272364, 2014/0363091, 2013/0017405, 2011/0293958, and 2008/0299391. A variety of materials (e.g., polymerizers) may be used as healing agents, including epoxy, polyurethane, urethane, fluoropolymer, polyvinyl chloride, polyimide, polyamide, acrylic, alkyd, silicone, phenolic resin, nitrocellulose, nylon, natural rubber, synthetic rubber, or a combination thereof. In some embodiments, photo-protected capsules containing a photopolymer composition are embedded (or dispersed) in an epoxy coating to form an autonomic self-healing material. The capsule shell wall is formulated to protect the photopolymer composition from electromagnetic exposure prior to rupturing of the microcapsule, so that the photopolymer composition (e.g., a photo-curable monomer composition) remains active and protected until triggered by mechanical or other sufficient damage to a region of the coating to cause rupturing of one or more of the microcapsules, which releases the photopolymer composition in the damaged region. When sufficient damage is inflicted on the coating, the one or more capsules will rupture, which allows the photopolymer composition to fill the damaged region. When the damaged region is exposed to electromagnetic light (e.g., of a similar intensity to sunlight), autonomic self-healing of the damaged coating is achieved. The curing of the microcapsule core composition heals the damaged coating and protects it from corrosion. The coating can be applied to numerous types of substrates (e.g., clean and prepared steel substrates).

In certain embodiments, the photopolymer composition is based on a photo-curable epoxy resin composition. The coatings have uniform thickness, are easy to source and manufacture, and allow for wide applications in industry. Similarly, the microcapsules sizes are relatively small when compared to the thickness of the coating. In certain embodiments, the size can be as small as 20 microns. This also allows for wider applications. In some embodiments, the photo-curable epoxy resin composition comprises bisphenol A epoxy resin, bisphenol F epoxy resin, novolac epoxy resin, aliphatic epoxy resin, cycloaliphatic epoxy resin, and/or glycidylamine epoxy resin. In certain particular embodiments, the photo-curable core composition comprises diglycidyl ether of bisphenol A (DGEBA) or diglycidyl ether of bisphenol F (DGEBF). In a certain embodiment, the photo-curable epoxy resin composition comprises an epoxy resin diluted with a low viscosity reactive diluent. In some embodiments, the low viscosity reactive diluent comprises ethyl hexyl glycidyl ether, trimethylol propane triglycidyl ether, phenyl glycidyl ether, or cyclohexane dimethanol diglycidyl ether. In one embodiment, the low viscosity reactive diluent comprises o-cresyl glycidyl ether (o-CGE). In one particular embodiment, the bisphenol-A epoxy resin composition comprises EPON 813™ (HEXION). Catalysts and initiators may also be present in the coating. The microcapsules can be mixed into a variety of polymer films, such as an epoxy resin film. In some embodiments, the epoxy resin film comprises zinc-pigmented epoxies, water-based epoxies, or DGEBA-based resins. In certain embodiments, the epoxy resin film comprises EPI-REZ™ 6520-WH-53 resin (HEXION) and EPIKURE™ 6870-W-53 (HEXION) curing agent.

The substrate can be anything designed to carry a load, such as a structural or non-structural (e.g., elastomer) substrate. A structural substrate is one that carries the load with minimal deflection. Structural substrates include metal, non-metal, ceramic, and polymeric materials. In certain embodiments, the structural substrate comprises a polymeric structural composite (PMC). PMCs are composed of high strength/stiffness fibers, held together by a polymer matrix material. Common examples include a carbon fiber composite, glass fiber, an epoxy resin, or a combination thereof. In one embodiment, the PMC comprises a combination of an epoxy resin with glass fiber or carbon fiber. The epoxy can be vacuum infused into the glass fiber or the carbon fiber to create a glass or carbon fiber reinforced epoxy composite. In other embodiments, the structural substrate is steel.

In other embodiments, protecting agents (e.g., anticorrosive, antibacterial, healing chemistries, etc.) can be encapsulated. Examples of corrosion inhibitors can be found in M. Zheludkevich, S. Poznyak, L. Rodrigues, D. Raps, T. Hack, L. Dick, T. Nunes, M. Ferreira, *Active protection coatings with layered double hydroxide nanocontainers of corrosion inhibitor, Corrosion Science* 52 (2) (2010) 602-611; A. Vimalanandan, L.-P. Lv, T. H. Tran, K. Landfester, D. Crespy, M. Rohwerder, *Redox-responsive self-healing for corrosion protection, Advanced materials* (Deerfield Beach, Fla.) 25 (48) (2013) 6980-6984; S. Garcia, H. Fischer, P. White, J. Mardel, Y. Gonzalez-Garcia, J. Mol, E. Hughes, *Self-healing anticorrosive organic coating based on an encapsulated water reactive silyl ester: Synthesis and proof of concept, Progress in Organic Coatings* 70 (2-3) (2011) 142-149. Examples of self-healing coatings can found in U.S. Pat. No. 7,723,405 and S. H. Cho, S. R. White, P. V. Braun, *Self-healing polymer coatings, Advanced Materials* 21 (6) (2009) 645-649; C. Suryanarayana, K. C. Rao, D. Kumar, *Preparation and characterization of microcapsules containing linseed oil and its use in self-healing coatings, Progress in Organic Coatings* 63 (1) (2008) 72-78.

A PDA coated capsule is illustrated in FIG. 1. Part of the capsule wall (outer shell) 12 is cut away to show a functional agent 10 core content contained therein. The capsule wall 12 comprises a PDA layer, which protects the encapsulated functional agent 10. The capsule ruptures or disintegrates when it has been sufficiently damaged by stimuli (e.g., by fatigue, impact or scratching). The functional agent 10 is only released (and de-protected) upon rupture or disintegration of the capsule.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described.

The singular forms "a," "an," and "the" include plural reference unless the context clearly dictates otherwise.

The claims may be drafted to exclude any optional element. This statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "at least one" and "one or more" are readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values (e.g., numbers recited in weight percentages and material sizes) proximate to the recited range that are equivalent in terms of the functionality of the individual ingredient, material, composition, or embodiment. The term about can also modify the end-points of a recited range as discussed above in this paragraph.

As will be understood by the skilled artisan, all numbers, including those expressing sizes of materials, quantities of ingredients, and properties, such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited herein are for illustration only and do not exclude other defined values or other values within defined ranges.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "autonomic polymer material" refers to automatically (without human or electronic control intervention) stopping, starting and adapting operation of the material depending on environmental or physical stimuli. For example, the objective of a self-healing material is to return undamaged functionality to the environmentally or physically damaged material without humans needing to know the damage ever occurred.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

A "sufficient amount" refers to an amount sufficient to bring about a recited effect, such as an amount of damage inflicted to a coating that is necessary to rupture one or more microcapsules, thereby releasing the agents contained therein. Thus, a "sufficient" amount generally means an amount that provides the desired effect.

All publications, patents, and patent applications mentioned in the specification are indicative of the level of those skilled in the art to which this invention pertains. These documents are herein incorporated by reference to the same extent as if each individual publication, patent, or patent application was specifically and individually indicated to be incorporated by reference. Nothing herein is to be construed as an admission that the present invention is not entitled to antedate such document by virtue of prior invention.

The design and operation of a PDA coated capsule was demonstrated in the following Examples. The following Examples are intended to illustrate the above invention and should not be construed as to narrow its scope. One skilled in the art will readily recognize that the Examples suggest many other ways in which the invention could be practiced. It should be understood that numerous variations and modifications can be made while remaining within the scope of the invention.

EXAMPLES

Materials o-dichlorobenzene (o-DCB), urea, ammonium chloride, resorcinol, formalin solution (37 w/v %), ammonium persulfate, dopamine hydrochloride, sodium phosphate monobasic monohydrate, sodium citrate dihydrate, tris (hydroxymethyl) aminomethane (TRIS), sodium hydroxide were used as received from Sigma Aldrich. The commercial polyurethane (PU) prepolymer, Desmodur L75, was obtained from Bayer Material Science and used as received. Ethylene-maleic anhydride (EMA) copolymer (Zemac-400) powder (Mw~400 kDa) was obtained from Vertellus and used as a 1.25 wt % aqueous solution.

1. Preparation of Microcapsules

The microcapsules were prepared by adapting conventional procedures. For example, see the procedures described in Caruso, M. M.; Blaiszik, B. J.; Jin, H.; Schelkopf, S. R.; Stradley, D. S.; Sottos, N. R.; White, S. R.; Moore, J. S., *Robust, Double-Walled Microcapsules for Self-Healing Polymeric Materials, ACS Appl. Mater. Interfaces* 2010, 2, 1195-1199; Blaiszik, B. J.; Caruso, M. M.; McIlroy, D. A.; Moore, J. S.; White, S. R.; Sottos, N. R., *Microcapsules Filled with Reactive Solutions for Self-Healing Materials, Polymer* 2009, 50, 990-997; U.S. Pat. No. 8,951,639. In one embodiment, PU/UF double layered shell wall capsules were prepared in a mixer via in situ interfacial polymerization of urea and formaldehyde (UF) in an oil-in-water emulsion. Urea (0.9 g), ammonium chloride (0.2 g), and resorcinol (0.09 g) were dissolved in 1.25 wt % EMA aqueous solution (60 mL). o-DCB (10 mL) that contains Desmodur L75 (0.33 g) was subsequently added into the aqueous phase. A fine emulsion was formed after 3 min of homogenization (Omni GLH) of the mixture. The emulsion was mechanically stirred at 800 rpm. After adding formalin solution (2.4 g), the emulsion was heated up to 55° C. and allowed to react for 4 h. Microcapsules were separated by centrifugation and then washed with water 3 times to remove the residual surfactant and unencapsulated shell wall particles. Free flowing microcapsules were obtained by freeze drying.

2. PDA Coating of Microcapsules

Two different methods were utilized to coat the microcapsules with PDA.

(i) In a first approach, microcapsules (0.2 g) were pre-dispersed in a pH 8.4 buffer solution (10 mL). Dopamine hydrochloride (0.04 g) was then added into a stirring solution. The solution turned brown within 20 min, indicating the polymerization of dopamine. After 1 day, the coated microcapsules were centrifuged, rinsed with water 3 times, and freeze dried to obtain free flowing powder. The pH 8.4 buffer contained 1 M TRIS in D.I. water. HCl was used to adjust the pH to 8.4.

(ii) In a second approach, microcapsules (0.2 g) were pre-dispersed in a pH 7.0 buffer solution (10 mL). Dopamine (0.04 g) and ammonium persulfate (0.04 g) were then added into a stirring solution. The solution turned brown within 10 min, indicating the polymerization of dopamine. After 1 day, the microcapsules were collected using the same procedure as above. The pH 7.0 buffer solution contained 1 M sodium phosphate monobasic monohydrate and 1 M sodium citrate dihydrate. NaOH was used to adjust the pH to 7.0.

Similarly, PDA polymer (no capsule) was made by adding dopamine (0.04 g) and ammonium persulfate (0.04 g) into a pH 7.0 buffer solution (10 mL) and reacting 1 day. The PDA polymer was centrifuged, rinsed with water 3 times, and dried under vacuum.

3. Characterization of Microcapsules

Microcapsule morphology was studied using SEM (Hitachi 4800) and TEM (Philips CM200). For SEM characterization, the microcapsules were placed on conductive carbon tape and sputter coated Au/Pd prior to imaging (accelerating voltage 10 kV). For the observation of a microcapsule shell wall, dried microcapsules were dispersed in epoxy resin (EPON™ 828 and 12 wt % DETA). After the epoxy resin was fully cured, the sample was microtomed to expose the shell wall of ruptured microcapsules. TEM was used to characterize the microcapsule shell wall.

The microcapsule shell wall components before and after PDA coating were characterized by Fourier Transform Infrared Spectroscopy (Thermo Nicolet NEXUS 670 FTIR). The microcapsules were ground with mortar and pestle to allow the release and evaporation of core liquid. Pellet samples were made with potassium bromide and stored under vacuum prior to testing in order to eliminate moisture.

Thermal analysis of microcapsules was performed on a Mettler-Toledo TGA 851. For dynamic experiments, the microcapsules were heated from 25 to 600° C., with 10° C./min heating rate, under nitrogen atmosphere. For isothermal studies, the microcapsules were heated up from 25 to 180° C. (10° C./min heating rate) and then held at 180° C. for 3 hours. The mass change was recorded throughout the entire experiment.

4. Solvent Stability of Microcapsules

For optical observation, uncoated and PDA coated microcapsules was added to desired solvents (5 wt % in water, pH 4 buffer solution, pH 10 buffer solution, acetone, ethyl acetate, and chloroform). After 3 days, an aliquot was taken and the morphology of microcapsules was observed under an optical microscope (Leica DMR Optical Microscope). In the cases of acetone, ethyl acetate, and chloroform, the images showed dried microcapsules. In water, pH 4 and pH 10 buffer solutions, the images showed dispersed microcapsules in aqueous media.

$^1$H-NMR method was used to quantify the percent core release of microcapsules in several solvents (acetone, ethyl acetate, and chloroform). Microcapsules (50 mg) were added to the desired solvent (1 g). After 3 days, hexyl acetate (20 mg) was added to the suspension as an internal standard. Subsequently, an aliquot was taken and filtered to remove the microcapsules. The filtered clear liquid was diluted by d-chloroform for $^1$H-NMR measurement. The released o-DCB concentration was calculated based on the integrated peak ratios of o-DCB and hexyl acetate in $^1$H-NMR spectra.

5. Results and Discussion

Figure 2:
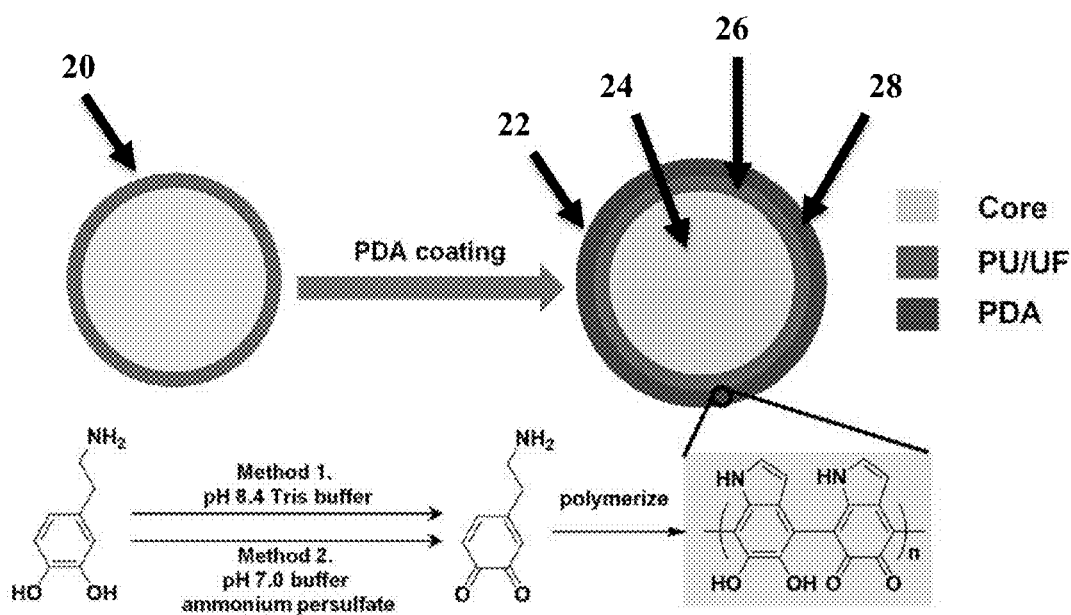
FIG. 2 shows two reaction schemes and images of the deposition and polymerization of dopamine on the surface of a capsule.

Microcapsules containing o-DCB were prepared by a combined in-situ/interfacial emulsion technique described above. Two different methods were used to form PDA coatings on microcapsule surfaces with coating conditions having differing solution pH values (FIG. 2). PDA is commonly prepared by the polymerization of dopamine hydrochloride in TRIS buffer solution at pH 8.4. Dreyer, D. R.; Miller, D. J.; Freeman, B. D.; Paul, D. R.; Bielawski, C. W., *Perspectives on Poly(dopamine)*, Chem. Sci. 2013, 4, 3796.

The catechol moieties in dopamine were oxidized to quinine and subsequently underwent polymerization to form PDA, accompanied by a color change from transparent to dark brown within 20 min. Two separate methods were tested: (i) in the first method, PDA was coated on microcapsule surfaces in an aqueous solution at pH 8.4; and (ii) in the second method, the PDA coating was formed in a neutral aqueous solution at pH 7.0 in the presence of an oxidant. Since the polymerization of dopamine does not typically occur at neutral pH, ammonium persulfate was added to oxidize the catechol groups to quinine groups and initiate the polymerization. Wei, Q.; Zhang, F.; Li, J.; Li, B.; Zhao, C., *Oxidant-Induced Dopamine Polymerization for Multifunctional Coatings*, Polym. Chem. 2010, 1, 1430-1433.

FIG. 2 shows the two methods for the polymerization of dopamine and deposition of PDA on core-shell microcapsule surfaces under the following conditions: (1) pH 8.4 buffer solution in the presence of TRIS; and (2) pH 7.0 buffer solution in the presence of ammonium persulfate. A pristine PU/UF walled capsule 20 is coated with PDA as described above. The resulting capsule 22 comprises a core content 24, a PU/UF shell wall 26, and a PDA coating 28 on top of the shell wall 26.

Figure 3:
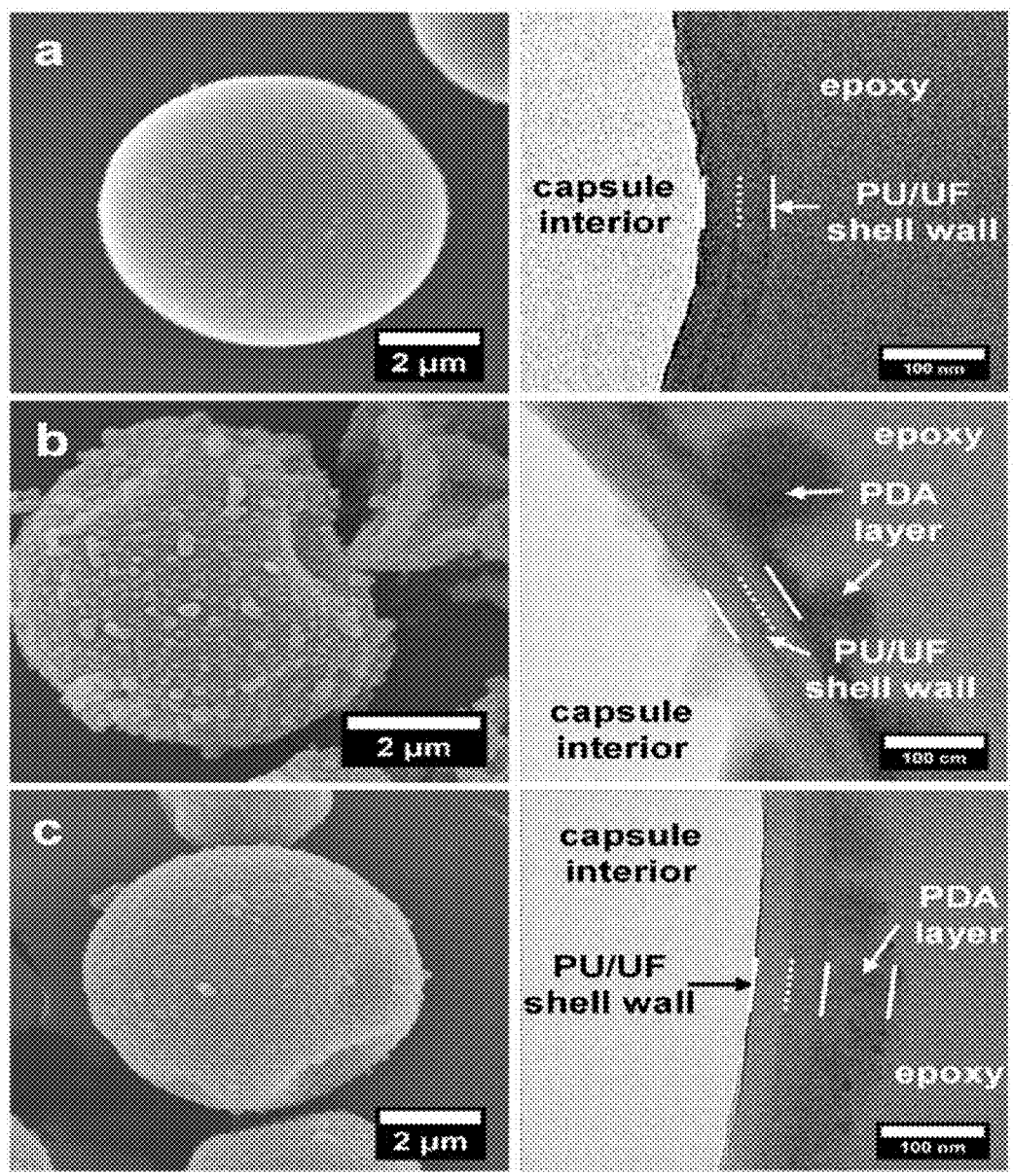
FIG. 3 shows SEM and TEM images of uncoated and PDA coated capsules.

The deposition of PDA on capsule surfaces can be seen in FIG. 3, which shows capsule morphology and shell wall cross-section images of three types of capsules subjected to different processing conditions: (a) SEM and TEM of cross-section of uncoated PU/UF microcapsule; (b) SEM and TEM of cross-section of PDA coated microcapsule prepared in pH 8.4 solution; (c) SEM and TEM of cross-section of PDA coated microcapsule prepared in pH 7.0 solution. In contrast to the smooth surface morphology of uncoated microcapsules ((a) of FIG. 3), PDA coated microcapsules have enhanced surface roughness, indicating the deposition of PDA. The microcapsules prepared in basic solution (pH 8.4) have an irregular shape and poor shell wall integrity ((b) of FIG. 3). It appears that the alkaline conditions cause the capsule shell wall to deteriorate, which leads to the release of o-DCB core into the aqueous media. We hypothesize that core leakage leads to a poor capsule surface for PDA polymerization, resulting in a rough PDA coating and less stable capsules. In stark contrast, the microcapsules prepared in a neutral pH (pH 7.0) buffer solution retained their spherical shape and uniform thickness ((c) of FIG. 3). The dimple of the capsule was caused by the exposure (~30 s) to the electron beam of SEM. The PDA coating was ca. 50 nm thick, similar to the thickness of the inner PU/UF layer. Only the PDA coated microcapsules prepared under neutral conditions (pH 7.0) were subject to further characterization studies.

Figure 4:
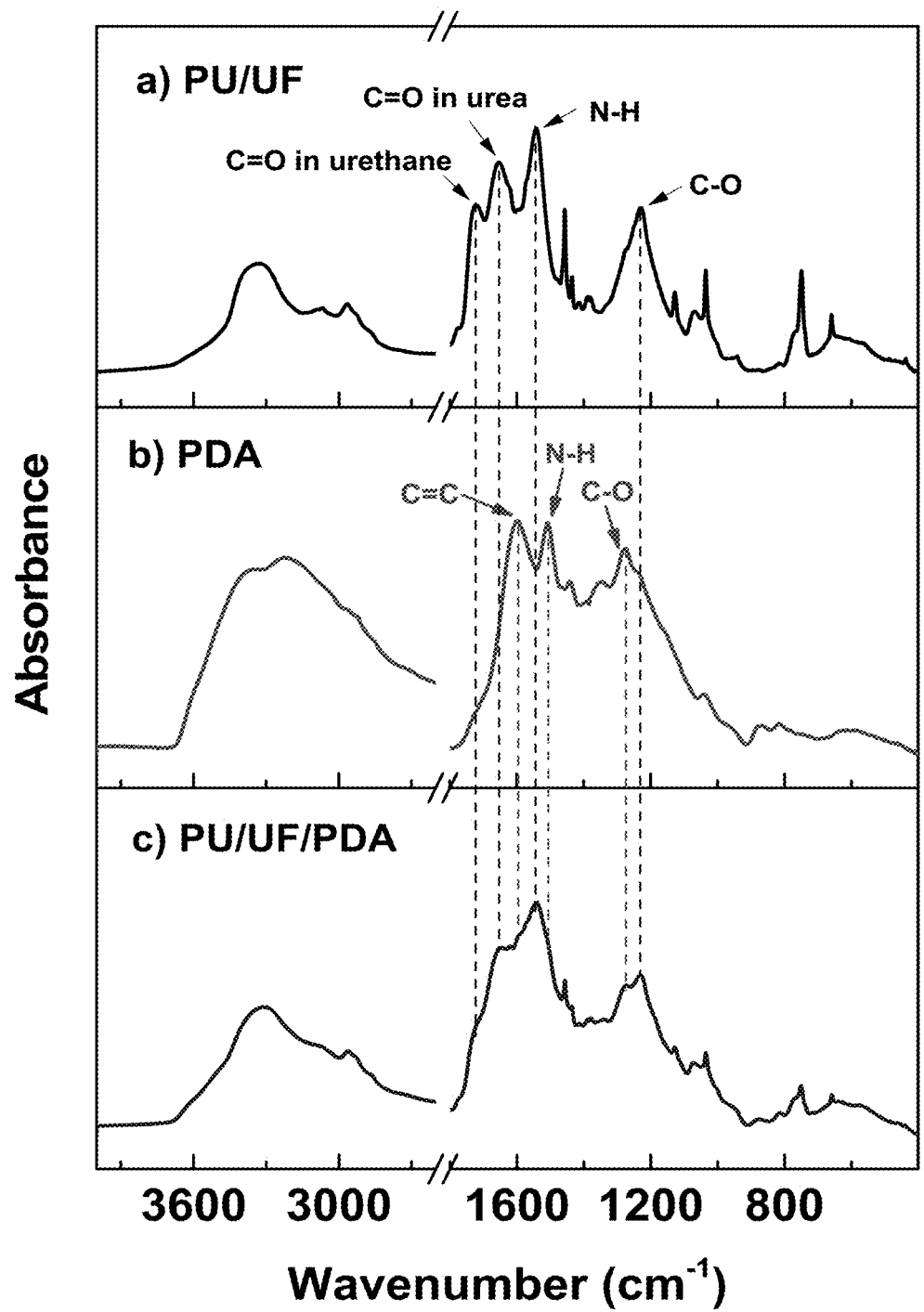
FIG. 4 shows FT-IR spectra of uncoated and PDA coated capsules.

The PDA coating on the microcapsules was confirmed by FT-IR measurements as shown in FIG. 4, which compares three different types of shell wall materials: (a) PU/UF from ground uncoated microcapsules; (b) PDA synthesized in pH 7.0 buffer solution; and (c) PU/UF/PDA from ground PDA coated microcapsules. The absorbance peaks in (c) of FIG. 4 are indicated by vertical black and red dotted lines corresponding to the absorbance peaks in neat PU/UF and PDA. The FT-IR spectrum of the PDA coated microcapsule shell wall showed the characteristic absorbance peaks of both PU/UF and PDA polymers. The absorbance peaks of PU/UF/PDA from 1800 to 1400 cm$^{-1}$ are the superposition of the absorbance peaks of PU/UF at 1723, 1653, 1543 cm$^{-1}$, and 1231 cm$^{-1}$ (C=O stretching from urethane, C=O stretching from urea, N—H scissoring, and C—O stretching, respectively) and the absorbance peaks of PDA at 1510, 1600 cm$^{-1}$, and 1274 cm$^{-1}$ (N—H scissoring, C=C stretching from the indole ring, and C—O stretching from phenolic moieties, respectively). Luo, R.; Tang, L.; Wang, J.; Zhao, Y.; Tu, Q.; Weng, Y.; Shen, R.; Huang, N, *Improved Immobilization of Biomolecules to Quinone-Rich Polydopamine for Efficient Surface Functionalization*, Colloids Surf, B 2013, 106, 66-73; Müller, M.; Keßler, B., *Deposition from Dopamine Solutions at Ge Substrates: An in Situ ATR-FTIR Study*, Langmuir 2011, 27, 12499-12505. The broad peak of PU/UF/PDA from 2700 to 3700 cm$^{-1}$ is an overlap of the peaks from PU/UF (O—H stretching, N—H stretching, aromatic and aliphatic C—H stretching) and PDA (hydrogen bonding, O—H stretching, N—H stretching, aromatic and aliphatic C—H stretching) spectra.

Figure 5:
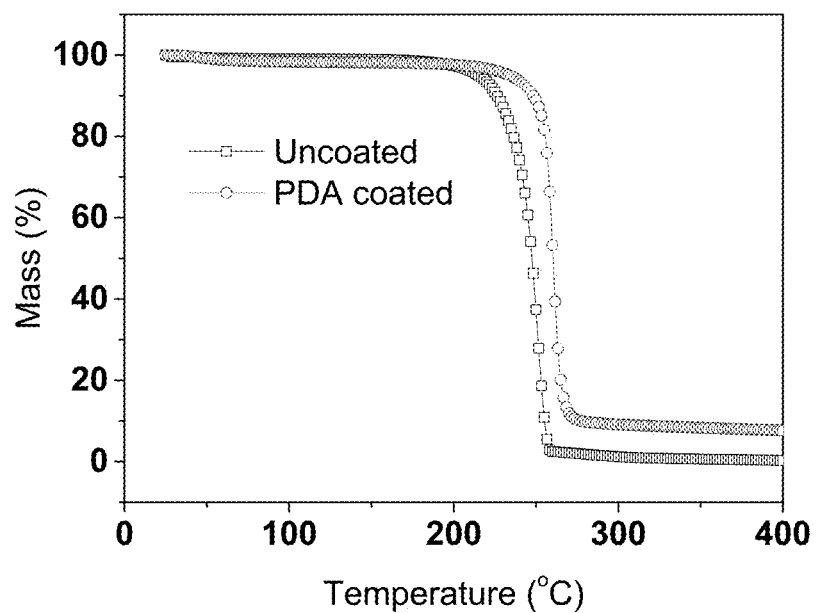
FIG. 5 shows thermal gravimetric analysis (TGA) spectra of uncoated capsules and PDA coated capsules made in pH 7.0 buffer solution.
Figure 5:
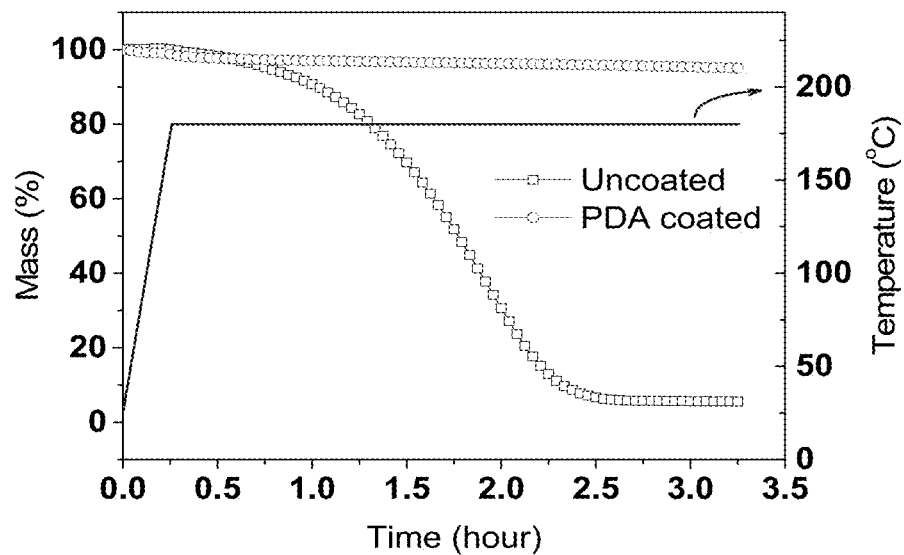
Figure 6:
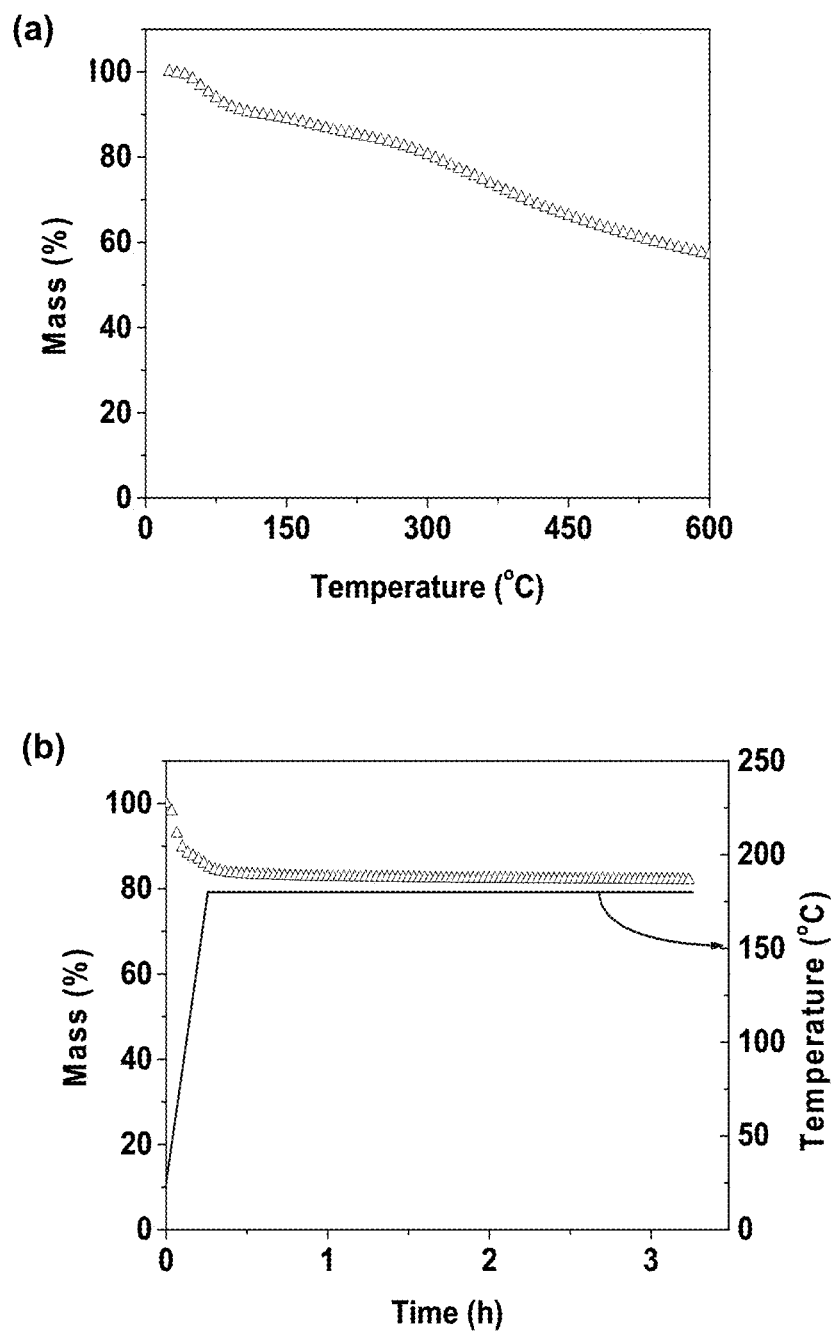
FIG. 6 shows TGA spectra of PDA polymer synthesized in pH 7.0 buffer solution.
Figure 7:
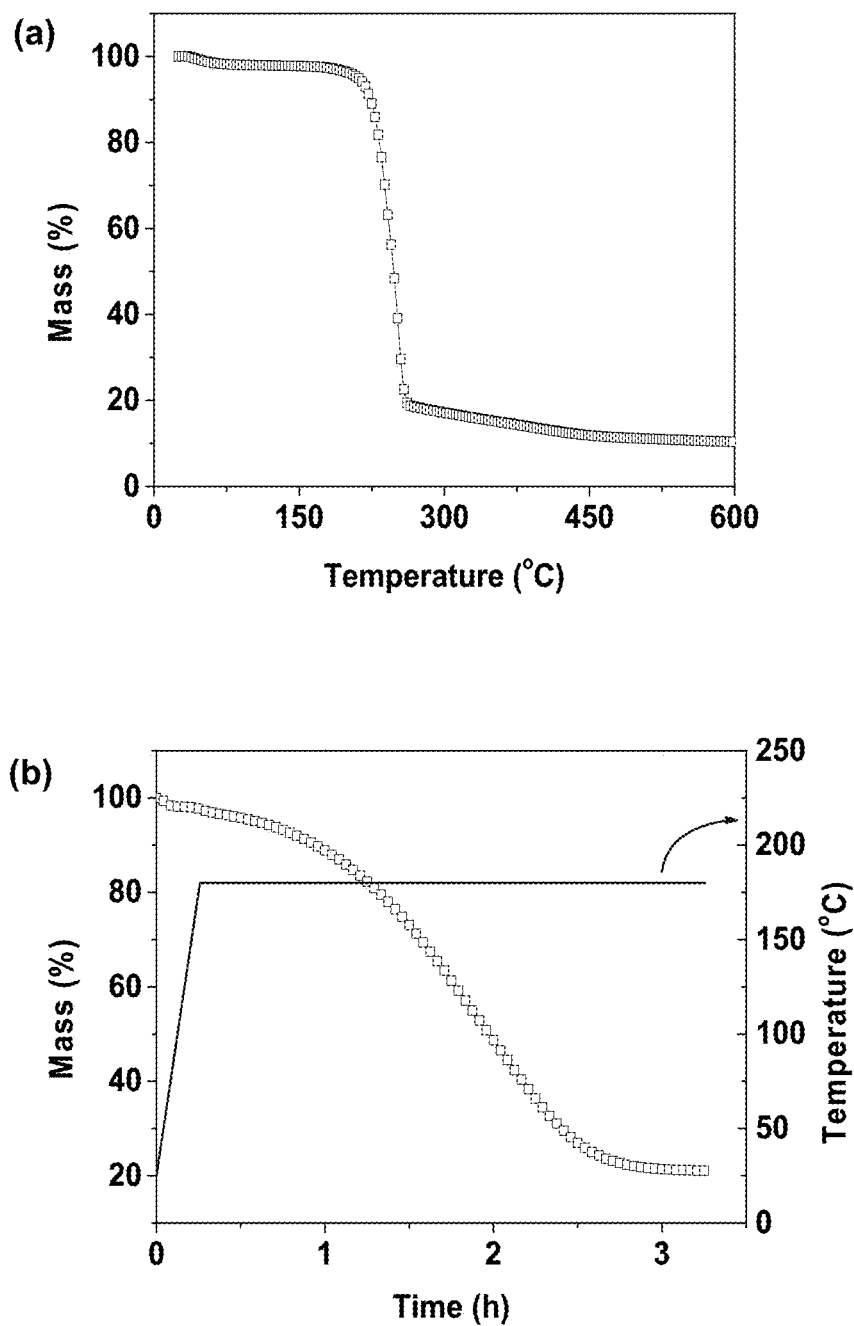
FIG. 7 shows TGA spectra of PDA coated capsules made in pH 8.4 buffer solution.

The thermal stabilities of uncoated microcapsules, PDA coated microcapsules (prepared by Methods 1 and 2), and PDA polymer were evaluated by thermal gravimetric analysis (TGA) under dynamic and isothermal conditions, which can be seen in FIGS. 5, 6, and 7: (a) dynamic scanning (25-400° C. or 25-600° C., 10° C./min) and (b) isothermal condition (180° C., 3 hours). In FIG. 5, the PDA coated microcapsules were prepared by Method 2 (pH 7.0 buffer solution). In FIG. 6, the PDA polymer was made in pH 7.0 buffer solution. In FIG. 7, the PDA coated microcapsules were prepared by Method 1 (pH 8.4 buffer solution).

The blue line shows the temperature profile. In the dynamic experiment ((a) of FIG. 5), weight loss of uncoated microcapsules was initiated at 225° C. due to rupture of the shell wall and evaporation of the o-DCB core content. For PDA coated microcapsules prepared by Method 2, the onset weight loss temperature increased by ~20° C. to 245° C. Above 200° C., o-DCB (b.p. 180° C.) was volatile. We hypothesize that the PDA shell wall was able to hold a higher vapor pressure of o-DCB than the PU/UF shell wall, postponing the microcapsule rupture temperature by ~20° C. Given that the remaining mass of plain PDA polymer at 600° C. is ca. 60 wt % ((a) of FIG. 6) and that the feed ratio of capsules to PDA monomers (5:1 by weight) for the coating process is 5:1 by weight, the ca. 10 wt % residue mass at 600° C. for PDA coated microcapsules comes from the PDA coating. Thermal stability was further studied by isothermal TGA of the microcapsules at 180° C. for 3 hours ((b) of FIG. 5). The weight loss for the uncoated microcapsules was 94.4 wt % at 180° C., leaving only the microcapsule shell wall. In contrast, the PDA coated microcapsules only lost 3.7% weight, showing good core retention ability at high temperature. Plain PDA polymer showed ca. 20 wt % weight loss within the first 20 min at 180° C. ((b) of FIG. 6), possibly due to the loss of trapped water.

In FIG. 7, we observed a sharp onset of weight loss at a temperature of 225° C. for PDA coated microcapsules prepared by Method 1 ((a) of FIG. 7). The weight loss in the isothermal TGA curve was ca. 80 wt % as prepared by Method 1 ((b) of FIG. 7) as opposed to 3.7 wt % weight loss for the capsules prepared by Method 2 ((b) of FIG. 5). Hence, the improvement of thermal stability of PDA coated capsules made by Method 1 was inferior to that of PDA coated capsules made by Method 2.

Figure 8:
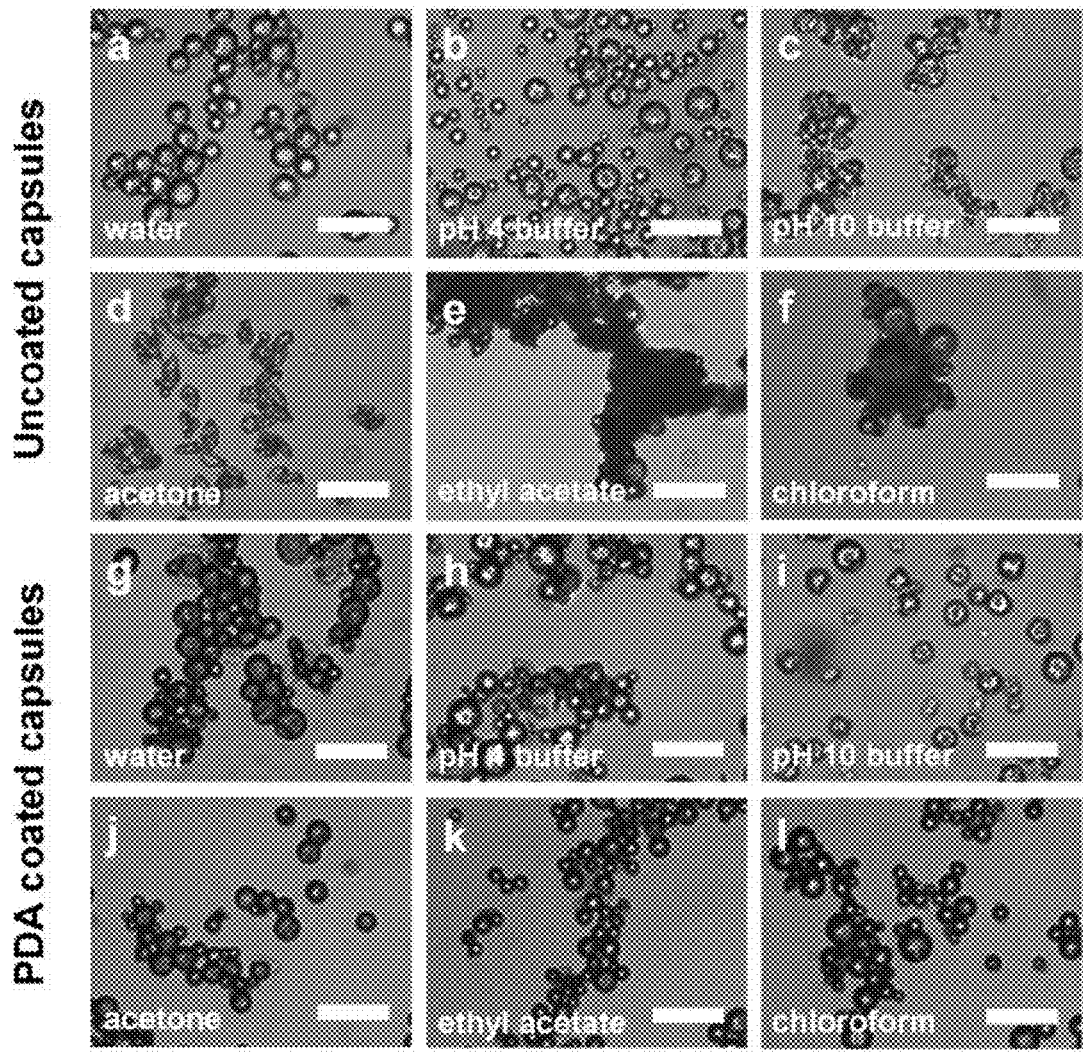
FIG. 8 shows optical images of uncoated and PDA coated capsules subjected to different processing conditions.

To evaluate the stability in solvent, we soaked the microcapsules in different organic solvents and aqueous solutions with different pH at room temperature. Optical images of the microcapsules after 3 days of immersion were taken and are shown in FIG. 8. After 3 days of immersion, optical images were taken of uncoated microcapsules ((a)-(c) of FIG. 8) and PDA coated microcapsules ((g)-(i) of FIG. 8) in neutral (pH 7.0), acidic (pH 4.0), and basic (pH 10.0) buffer solutions. The uncoated microcapsules ((d)-(f) of FIG. 8) and PDA coated microcapsules ((j)-(l) of FIG. 8) were immersed in different solvents. The scale bar is 20 µm for all images. In aqueous systems, both uncoated and PDA coated microcapsules showed good survival properties in acidic (pH 4) and neutral solutions. However, the uncoated microcapsules deflated in pH 10 solution and lost core content, while the PDA coated microcapsules retained the majority of their core content under the same conditions. In organic solvents (acetone, ethyl acetate, and chloroform), the uncoated microcapsules were not able to maintain their core content and significant deflation and agglomeration were observed ((a)-(c) of FIG. 8). In contrast, the PDA coated microcapsules ((g)-(i) of FIG. 8) remained dispersed and spherical, suggesting good solvent stability.

Figure 9:
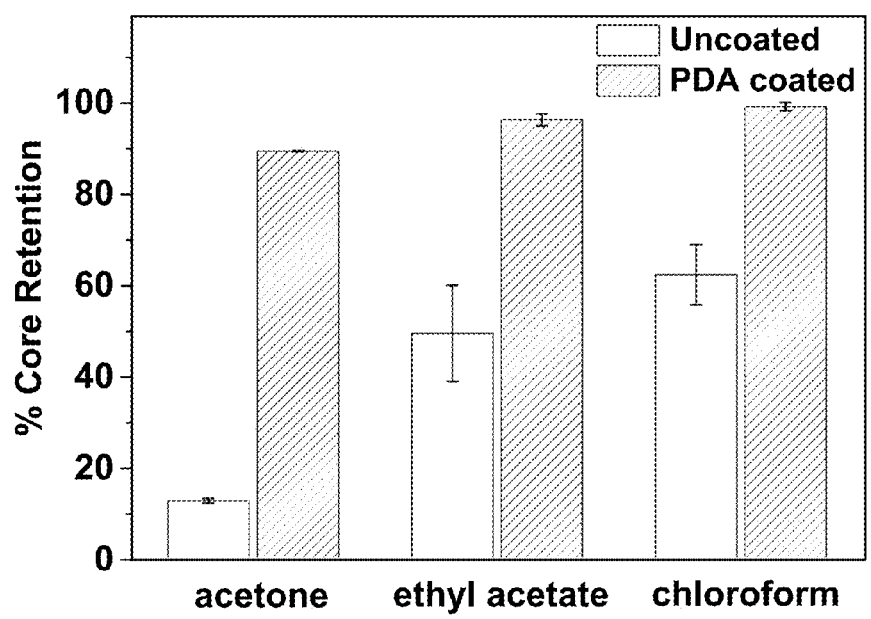
FIG. 9 shows $^1$-NMR data of o-DCB core content retention in uncoated and PDA coated capsules after immersion in different organic solvents.

FIG. 9 shows the weight percent of o-DCB core release of the microcapsules in different organic solvents after 3 days of immersion was quantified by $^1$H-NMR. The PDA coated capsules retained over 90% of the o-DCB core in acetone, ethyl acetate, and chloroform, while the uncoated capsules lost from 40 to 90% of core content depending on the solvent.

The data reported in the experimental section shows that microcapsules prepared by coating core-shell microcapsules with PDA polymer film exhibited superior thermal and solvent stabilities. The PDA coating effectively limited the diffusion of core liquid through the microcapsule shell wall at elevated temperature (180° C.). Reduced permeability of capsule shell wall was also observed in common organic solvents as well as in a basic aqueous solution. The PDA protective coating served as an effective barrier for o-DCB core diffusion. The improved thermal and solvent stabilities of the PDA coated microcapsules make them promising candidates for self-healing polymers and composites cured at elevated temperatures, and also for a variety of applications where exceptional capsule stability is required.

What is claimed is:

1. A core-shell microcapsule consisting of:
    a) a coating of polydopamine (PDA) on a shell wall of a microcapsule, wherein the microcapsule has enhanced environmental stability, and the shell wall optionally consists of poly(urea formaldehyde) (PUF), poly(urethane) (PU), or a combination thereof; and
    b) an optional encapsulated functional liquid;
wherein the functional liquid optionally consists of a healing material, pharmaceutical drug, food additive, or a combination thereof.

2. The microcapsule of claim 1 where the microcapsule contains the encapsulated functional liquid.

3. The microcapsule of claim 1 where the shell wall consists of poly(urea formaldehyde) (PUF), poly(urethane) (PU), or a combination thereof.

4. The microcapsule of claim 3 where the shell wall consists of a dual-layered poly(urea formaldehyde)/poly(urethane) (PUF/PU).

5. The microcapsule of claim 2 where the functional liquid consists of a healing material, pharmaceutical drug, food additive, or a combination thereof.

6. The microcapsule of claim 5 where the microcapsule is dispersed in an epoxy resin film.

7. The microcapsule of claim 6 where the microcapsule is coated onto a substrate.

8. The microcapsule of claim 6 where the PDA coating adheres or bonds to epoxy.

9. The microcapsule of claim 1 where the PDA coating has a thickness similar to the thickness of the core-shell wall.

10. The microcapsule of claim 1 where the PDA coating has a thickness of about 50 nM.

11. The microcapsule of claim 4 where the PDA coating has a thickness similar to the thickness of the PUF/PU dual-layered wall.

12. The microcapsule of claim 2 where the polydopamine (PDA) coated microcapsule retains the functional liquid by inhibiting diffusion from the core.

13. The microcapsule of claim 12 where the PDA coated microcapsule has enhanced thermal stability relative to a microcapsule not coated with PDA.

14. The microcapsule of claim 12 where the onset weight loss temperature of the PDA coated microcapsule increases by about 20° C. relative to a microcapsule not coated with PDA.

15. The microcapsule of claim 12 where the PDA coated microcapsule retains a functional agent at higher vapor pressures relative to a microcapsule not coated with PDA.

16. The microcapsule of claim 12 where the PDA coated microcapsule has enhanced solvent stability relative to a microcapsule not coated with PDA.

17. The microcapsule of claim 16 where the PDA coated microcapsule is stable in organic solvents relative to a microcapsule not coated with PDA.

18. The microcapsule of claim 16 where the PDA coated microcapsule is stable in aqueous solvents relative to a microcapsule not coated with PDA.

19. The microcapsule of claim 18 where the PDA coated microcapsule is stable at acidic pH, relative to a microcapsule not coated with PDA.

20. The microcapsule of claim 18 where the PDA coated microcapsule is stable at alkaline pH, relative to a microcapsule not coated with PDA.

21. A method of coating polydopamine onto the shell wall of a core-shell microcapsule of claim 1, the method comprising polymerizing dopamine monomers on the shell-wall of a core-shell microcapsule, where the microcapsule and dopamine monomers are in an aqueous buffer solution and the aqueous buffer solution has:
   (a) an acidic or about neutral pH, and adding an oxidant to the buffer solution; or
   (b) a basic pH;
whereby the dopamine monomers polymerize on the shell wall of the microcapsule.

22. The method of claim 21 where the oxidant is ammonium persulfate.

23. The method of claim 21 where the microcapsule encapsulates a functional liquid.

* * * * *

UNITED STATES PATENT AND TRADEMARK OFFICE
CERTIFICATE OF CORRECTION

PATENT NO. : 9,943,487 B2
APPLICATION NO. : 15/165520
DATED : April 17, 2018
INVENTOR(S) : Scott R. White et al.

Page 1 of 1

It is certified that error appears in the above-identified patent and that said Letters Patent is hereby corrected as shown below:

On the Title Page

Item [72], please delete "Marta B. Baginska, Urbana, IL (US)" and insert -- Marta B. Elleby, Urbana, IL (US) -- therefor.

Signed and Sealed this
Third Day of July, 2018

Andrei Iancu
*Director of the United States Patent and Trademark Office*